United States Patent [19]

Schouteeten et al.

[11] Patent Number: 5,354,897
[45] Date of Patent: Oct. 11, 1994

[54] PROCESS FOR OBTAINING ORTHOHYDROXYMANDELIC ACID AND ITS SALTS

[75] Inventors: Alain Schouteeten, Ezanville; Yani Christidis, Paris, both of France

[73] Assignee: Societe Francaise Hoechst, Puteaux, France

[21] Appl. No.: 15,429

[22] Filed: Feb. 12, 1993

[30] Foreign Application Priority Data

Feb. 12, 1992 [FR] France .................... 92 01565

[51] Int. Cl.$^5$ ............................................. C07C 59/48
[52] U.S. Cl. .................................................. 562/470
[58] Field of Search ........................................ 562/470

[56] References Cited

FOREIGN PATENT DOCUMENTS 0023459 2/1981
2638740 5/1990 France .

Primary Examiner—Paul J. Killos
Attorney, Agent, or Firm—Browdy and Neimark

[57] ABSTRACT

Preparation process for orthohydroxymandelic acid, as well as its salts, in which glyoxylic acid is reacted with phenol in the presence of a tertiary amine and catalytic quantities of trivalent metal cations, in order to obtain the expected product which is isolated and, if desired, salified.

20 Claims, No Drawings

PROCESS FOR OBTAINING ORTHOHYDROXYMANDELIC ACID AND ITS SALTS

The present invention relates to a process for obtaining orthohydroxymandelic acid and its salts.

Orthohydroxymandelic acid is widely described in the literature, and it is an invaluable intermediate for accessing orthohydroxyphenylacetic acid which is commonly used today for obtaining molecules having useful therapeutic or phytopathological properties.

Orthohydroxymandelic acid is not known in the pure crystallized state. It was isolated in the form of an oil and it was characterized notably by its diacetyl derivative. (R. HOWE et al, J. Chem. Soc., 1967, 2510–2514).

It is known that glyoxylic acid condenses with phenol in an alkaline aqueous medium leading to a mixture of ortho- or parahydroxymandelic acids, as well as to hydroxybenzenediglycolic acids substituted in positions 2,4 and 2,6.

It is also known that in an alkaline aqueous medium, glyoxylic acid undergoes dismutation according to Cannizzaro's reaction into oxalic and glycolic acids. Shouteeten and Christidis have shown that by reacting glyoxylic acid with phenol for a few minutes, at high temperature, in an alkaline aqueous medium, it was possible to minimise the Cannizzaro's reaction and to enhance the condensation reaction and in this way be able to achieve a yield of 70 to 85% of parahydroxymandelic acid (French Patent No. 2440350).

Furthermore, it is known how to prepare parahydroxymandelic acid with good selectivity, in a quasi anhydrous medium, by reacting glyoxylic acid with phenol, in the presence of an excess of a suitable tertiary amine, such as tributylamine (French Patent No. 2638740).

Recently, A. J. Hoefnagel et al, Rec. Trav. Chem., 107, 242–7 (1988), have shown that the condensation of glyoxylic acid with phenol could be catalyzed by certain metal ions and, that by operating in a dilute aqueous medium, at pH=5, at 100° C., in the presence of trivalent metal ions such as aluminium, chromium, iron, it was possible to obtain high selectivities in the ortho position.

However, due to on the one hand a significant dilution which gives rise to low productivity and on the other hand the obtaining of a high level of disubstituted products which leads to complex mixtures from which it is then difficult to isolate the sought orthohydroxymandelic acid, this process is not economical on an industrial scale.

In order to overcome these disadvantages, the Applicant has discovered with astonishment a process for obtaining orthohydroxymandelic acid, from glyoxylic acid and phenol, which leads simultaneously to good selectivity and to high yield and productivity.

According to the invention the orthohydroxymandelic acid, as well as its salts, is prepared by a process characterized in that glyoxylic acid is reacted with phenol, in the presence of a tertiary amine and catalytic quantities of trivalent metal cations, in order to obtain the expected orthohydroxymandelic acid which is isolated or, if desired, salified.

The tertiary amine is chosen from the tertiary amines, which preferably are liquid or gaseous at ambient temperature, such as the amines, or their mixture in variable proportions, of general formula (I) $N(R_1)(R_2)(R_3)$ in which $R_1$, $R_2$ and $R_3$, being identical or different, represent a linear or branched $C_1$–$C_{10}$ alkyl radical or a $C_2$ alkanol radical. As tertiary amines, the following can be mentioned: trimethylamine, triethylamine, tributylamine, trierhanoiamine, mixtures of $C_8$–$C_{10}$ tertiary amines marketed by the Applicant under the name HOSTAREX ® A 327. Preferably, the amine of general formula (I) is tributylamine.

Suitable trivalent metal cations include the following cations: aluminium (III), chromium (III), iron (III), gallium (III), indium (III), thallium (III), ruthenium (III), scandium (III), but preferably, the chromium (III), iron (III), aluminium (III) cations and quite particularly the latter.

In the advantageous conditions for implementing the invention, the process described above is carried out in the following manner:

at a temperature greater than or equal to 50° C., advantageously at a temperature greater than 100° C., at atmospheric pressure, in the presence of tributylamine, with a molar ratio of phenol to glyoxylic acid greater than 1, advantageously greater than 4, in a quasi anhydrous medium, i.e. a concentrated aqueous medium, with a molar ratio of tertiary amine to glyoxylic acid comprised between 0.8 and 1.2, advantageously between 0.9 and 1.1, in the presence of aluminium (III), chromium (III) or iron (III) cations, preferably in the presence of aluminium (III) cations, with a molar ratio of metal cations to glyoxylic acid comprised between 0.001 and 0.1, advantageously with a ratio equal to 0.05, with the glyoxylic acid in aqueous solution at a concentration by weight of greater than 50%, advantageously with an aqueous solution of glyoxylic acid at 66% by weight.

Salification may be carried out according to techniques well known to a man skilled in the art, for example, by using an alkaline hydroxide, notably sodium hydroxide.

The condensation reaction of the glyoxylic acid with phenol is advantageously monitored by chromatographic analysis of a sample taken regularly from the reaction medium. The chromatographic analysis can be carried out, in particular, as described by A. J. Hoefnagel et al. (already mentioned).

When the reaction is completed, that is to say when the glyoxylic acid employed is completely consumed, the sought orthohydroxymandelic acid is isolated from the reaction medium by known methods. Advantageously, the cooled reaction medium is diluted with an aqueous solution of sodium hydroxide, then it is washed with a non-miscible organic solvent to eliminate the unconverted phenol and the tertiary amine used. The residual aqueous solution containing the salified orthohydroxymandelic acid is then either used as it is to prepare the orthohydroxyphenylacetic acid for example by reaction with a hydrogen donor agent such as formic acid in the presence of a hydrogen transfer catalyst such as palladium on charcoal, preferably in a solvent such as water or acetic acid, or acidified to pH - 1.5 with concentrated hydrochloric acid, then washed with ethyl acetate to extract the orthohydroxymandelic acid; the organic phases of the extraction are then concentrated under reduced pressure, then the residual oil is dissolved in the minimum quantity of ethanol, left so that the pure sodium orthohydroxymandelate crystals deposit when they are treated with a solution of sodium hydroxide in ethanol.

Examples 1–10 of the process according to the invention, as well as the comparison examples C1–C11, were carried out under agitation, under an inert atmosphere, at a temperature Θ for a time t (values given in table I). The tests carried out starting with sodium glyoxylate, designated NaGA, were carried out at a pH adjusted to 5 by the addition if necessary of a concentrated aqueous solution of sodium hydroxide. The number of mmoles of orthohydroxymandelic acid, designated N, of parahydroxymandelic acid, designated M, and of 2,4- and 2,6-hydroxybenzenediglycolic acid, designated P, were determined by high pressure liquid chromatography according to the protocol given by A. J. Hoefnagel (already mentioned), but the peak identified as corresponding to the product disubstituted in position 2,6 corresponds in reality to the product disubstituted in position 2,4.

The selectivity of the reaction, designated S, is calculated according to equation 1, the rate of disubstitution, designated R, is calculated according to equation 2 and the yield Y is calculated according to equation 3 in which L signifies the number of mmoles of free or salified glyoxylic acid employed. In the tests L is equal to 100.

$$S = \frac{100N}{M + N + 2P} \quad \text{(equation 1)}$$

$$R = \frac{P100}{M + N + 2P} \quad \text{(equation 2)}$$

$$Y = \frac{(M + N + 2P)100}{L} \quad \text{(equation 3)}$$

Comparison example C9 is the reproduction of Example 1 of the Patent FR 2638740 carried out in the presence of aluminium sulphate.

In Table I the abbreviations used have the following meaning:

GA : Glyoxylic acid expressed as 100%
NaGA : Sodium glyoxylate expressed as 100%
n : Nature, either of the catalyst or the amine used
d : Dose expressed in mmoles
Θ : Temperature expressed in degrees Celsius
t : Time expressed in minutes
S : Selectivity
R : Rate of disubstitution
Y : Yield calculated relative to the glyoxylic acid used
A : Tributylamine
B : Chromium (III) chloride crystallized with 6 moles of water M.W.=266.45
D : Aluminium sulphate crystallized with 18 moles of water M.W.=666.42
F : Iron (III) chloride, M.W.=162.21
NM : Non-measurable
$H_2O$ : water—when the catalyst used contains water of crystallization, this water is not included in the values indicated in this column.

Examination of table I allows the following conclusions to be drawn:

The tests carried out in dilute aqueous medium do not allow the formation of disubstituted products with the phenol to be avoided, even in the presence of an excess of phenol relative to the glyoxylic acid (C1–C5).

The tests carried out with an excess of tertiary amine relative to the glyoxylic acid, and in the presence of a trivalent metal cation, do not allow a selectivity in para position to be obtained (C9).

The tests carried out with sodium glyoxylate in the presence of a trivalent metal cation and an excess of phenol, but in a quasi anhydrous medium do not allow a significant disubstitution rate to be obtained (C6).

TABLE I

| | GA (mmoles) | NaGA (mmoles) | Phenol (mmoles) | $H_2O$ (mmoles) | Catalyst nature | Catalyst dose (mmoles) | n | Amine d (mmole) | Θ (°C.) | t (min) | S (%) | R (%) | Y (%) |
|---|---|---|---|---|---|---|---|---|---|---|---|---|---|
| | | | | | EXAMPLES 1–10 | | | | | | | | |
| 1 | 100 | 0 | 800 | 210 | D | 5 | A | 95 | 50 | 465 | 86.5 | NM | 100 |
| 2 | 100 | 0 | 800 | 210 | D | 5 | A | 95 | 80 | 120 | 86 | NM | 98 |
| 3 | 100 | 0 | 800 | 210 | D | 5 | A | 95 | 80 | 180 | 86 | NM | 98 |
| 4 | 100 | 0 | 800 | 210 | D | 5 | A | 95 | 100 | 30 | 87.5 | NM | 94 |
| 5 | 100 | 0 | 800 | 210 | D | 5 | A | 95 | 115 | 9 | 86.7 | NM | 91 |
| 6 | 100 | 0 | 800 | 210 | D | 5 | A | 95 | 115 | 19 | 86 | NM | 91 |
| 7 | 100 | 0 | 800 | 210 | F | 10 | A | 95 | 100 | 5 | 87 | NM | 92 |
| 8 | 100 | 0 | 800 | 210 | F | 2 | A | 95 | 100 | 30 | 84.5 | NM | 99 |
| 9 | 100 | 0 | 800 | 210 | F | 1 | A | 95 | 100 | 60 | 73.5 | NM | 99 |
| 10 | 100 | 0 | 800 | 210 | B | 1.25 | A | 95 | 100 | 120 | 59 | NM | 97 |
| | | | | | COMPARISON EXAMPLES 1–11 | | | | | | | | |
| C1 | 0 | 100 | 100 | 9840 | D | 5 | | 0 | 100 | 240 | 44 | 20 | 75 |
| C2 | 0 | 100 | 200 | 9840 | D | 5 | | 0 | 100 | 240 | 55 | 15 | 95 |
| C3 | 0 | 100 | 400 | 9840 | D | 5 | | 0 | 100 | 240 | 70 | 6.4 | 98 |
| C4 | 0 | 100 | 500 | 9840 | D | 5 | | 0 | 100 | 240 | 76 | 6.5 | 98 |
| C5 | 0 | 100 | 600 | 9840 | D | 5 | | 0 | 100 | 240 | 72 | 6.4 | 98 |
| C6 | 0 | 100 | 800 | 120 | D | 5 | | 0 | 100 | 240 | NM | NM | 2 |
| C7 | 0 | 100 | 200 | 9840 | D | 5 | | 0 | 100 | 360 | 69 | 10.7 | 87 |
| C8 | 0 | 100 | 200 | 9840 | D | 5 | | 0 | 80 | 1200 | 52.5 | 11.2 | 98 |
| C9 | 100 | 0 | 800 | 210 | D | 5 | A | 150 | 100 | 60 | 19 | NM | 97 |
| C10 | 0 | 100 | 500 | 9840 | F | 10 | | 0 | 100 | 90 | 49 | 7.4 | 94 |
| C11 | 0 | 100 | 500 | 9840 | B | 1.25 | | 0 | 100 | 240 | 76 | 3 | 91 |

We claim:

1. Preparation process for orthohydroxymandelic acid, as well as its salts, comprising
reacting glyoxylic acid with phenol in a concentrated aqueous medium in the presence of tertiary amine and catalytic quantities of trivalent metal cations and wherein said concentrated aqueous medium consists essentially of said glyoxylic acid in aqueous solution at a concentration by weight greater than 50%, said phenol, said tertiary amine and said trivalent metal cations.

isolating the resultant product and, optionally salifying said product.

2. Process according to claim 1, characterized by the fact that the tertiary amine is liquid or gaseous at ambient temperature.

3. Process according to claim 2, characterized by the fact that the tertiary amine is of general formula (I)

$$N(R_1)(R_2)(R_3) \tag{I}$$

in which $R_1$, $R_2$ and $R_3$, being identical or different, have a linear or branched $C_1$–$C_{10}$ alkyl radical or a $C_2$ alkanol radical.

4. Process according to claim 3, characterized by the fact that the amine of general formula (I) is tributylamine.

5. Process according to claim 1, characterized by the fact that the trivalent metal cation is chosen from the group constituted by aluminium, chromium, iron.

6. Process according to claim 5, characterized by the fact that the trivalent metal cation is the aluminium cation.

7. Process according to claim 1, characterized by the fact that it is carried out at a temperature greater than or equal to 50° C.

8. Preparation process for sodium orthohydroxymandelate according to claim 1, characterized by the fact that it is obtained by the salification of orthohydroxymandelic acid with sodium hydroxide.

9. Process according to claim 2, characterized by the fact that the trivalent metal cation is chosen from the group constituted by aluminum, chromium, iron.

10. Process according to claim 3, characterized by the fact that the trivalent metal cation is chosen from the group constituted by aluminum, chromium, iron.

11. Process according to claim 4, characterized by the fact that the trivalent metal cation is chosen from the group constituted by aluminum, chromium, iron.

12. Process according to claim 11, characterized by the fact that it is carried out at a temperature greater than or equal to 50° C.

13. Process according to claim 10, characterized by the fact that it is carried out at a temperature greater than or equal to 50° C.

14. Process according to claim 9, characterized by the fact that it is carried out at a temperature greater than or equal to 50° C.

15. Process according to claim 5, characterized by the fact that it is carried out at a temperature greater than or equal to 50° C.

16. Process according to claim 4, characterized by the fact that it is carried out at a temperature greater than or equal to 50° C.

17. Process according to claim 3, characterized by the fact that it is carried out at a temperature greater than for equal to 50° C.

18. Process according to claim 2, characterized by the fact that it is carried out at a temperature grater than or equal to 50° C. said glycoxylic acid is provided in said concentrated aqueous medium as sodium glyoxylate, and said concentrated aqueous medium has a pH of about 5.

19. Preparation process for sodium orthohydroxymandelate according to claim 9, characterized by the fact that it is obtained by the salification of orthohydroxymandelic acid with sodium hydroxide.

20. Preparation process for sodium orthohydroxymandelate according to claim 7, characterized by the fact that it is obtained by the salification of orthohydroxymandelic acid with sodium hydroxide.

* * * * *